US007074491B2

(12) United States Patent
Liu et al.

(10) Patent No.: US 7,074,491 B2
(45) Date of Patent: Jul. 11, 2006

(54) POLAR SILANES FOR BINDING TO SUBSTRATES AND USE OF THE BOUND SUBSTRATES

(75) Inventors: Xiaodong Liu, Cupertino, CA (US); Andrei V. Bordunov, Campbell, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 182 days.

(21) Appl. No.: 10/702,109

(22) Filed: Nov. 4, 2003

(65) Prior Publication Data

US 2005/0095440 A1    May 5, 2005

(51) Int. Cl.
   *C07F 7/10*      (2006.01)
   *C07F 7/18*      (2006.01)
(52) U.S. Cl. .................. 428/447; 556/413; 556/415; 556/465
(58) Field of Classification Search ............... 556/413, 556/415, 465; 428/447
See application file for complete search history.

(56) References Cited

U.S. PATENT DOCUMENTS

| 3,175,993 | A | * | 3/1965 | Weyenberg ............... 528/27 |
| 4,017,528 | A | * | 4/1977 | Unger et al. ............. 556/457 |
| 4,211,729 | A | * | 7/1980 | Marquardt et al. ........ 525/106 |
| 4,623,740 | A | | 11/1986 | Buder et al. |
| 4,705,725 | A | | 11/1987 | Glajch et al. |
| 4,990,641 | A | | 2/1991 | Kabeta et al. |
| 5,019,637 | A | | 5/1991 | Panster et al. |
| 5,075,459 | A | | 12/1991 | Kabeta et al. |
| 5,374,755 | A | * | 12/1994 | Neue et al. ............... 556/400 |
| 6,183,867 | B1 | * | 2/2001 | Barthel et al. ............ 428/403 |
| 6,262,216 | B1 | | 7/2001 | McGall |
| 6,268,456 | B1 | * | 7/2001 | Gregorovich et al. ....... 528/35 |
| 6,429,275 | B1 | * | 8/2002 | McGall et al. ............ 528/10 |
| 6,528,167 | B1 | * | 3/2003 | O'Gara ................... 428/405 |
| 6,645,378 | B1 | * | 11/2003 | Liu et al. ................ 210/198.2 |
| 6,800,777 | B1 | * | 10/2004 | Arkles et al. ............. 556/400 |

FOREIGN PATENT DOCUMENTS

| DE | 2 250 921 | 4/1974 |
| EP | 0 136 680 A2 | 4/1985 |
| JP | 11-335380 | 5/1998 |
| JP | 2001-115130 | 4/2001 |
| WO | WO 94/00408 A1 | 1/1994 |
| WO | WO 94/09013 A1 | 4/1994 |
| WO | WO 95/15740 A1 | 6/1995 |
| WO | WO 00-21967 A1 | 4/2000 |
| WO | WO 00/45951 A1 | 8/2000 |

OTHER PUBLICATIONS

Kirkland, J.J., et al., "Bidentate Silane Stationary Phases for Reversed-Phase High-Performance Liquid Chromatography," *Anal. Chem.* 70(20):4344-4352 (Oct. 1998).
Bassindale, A., et al., "Bis-halo N,N-bisdimethylsilylmethylacetamides as dynamic probes for the effect of coordination on reactivity at silicon," *J. Chem. Soc. Chem. Commun.* 4:352-353 (1993).
Kar, S., et al., "Synthesis and chemical reactivity of α-Oxo aldehyde-supported silicas," *Eur. J. Org. Chem.* 11:4132-4139 (Nov. 2003).
Oviatt, H., et al., "Applications of organic bridged polysilsesquioxane xerogeis to nonlinear optical materials by the Sol-Gel method," *Chem. Mater.* 7(3):493-498 (Mar. 1995).
Pirkle, W., et al., "Chiral stationary phase design: a study in optimization," *J. High Res. Chromatogr.* 17(9):629-633 (Sep. 1994).
Villamo, O., et al., "Hybrid organic-inorganic membranes containing a fixed thio ether complexing agent for the facilitated transport of silver versus copper ions," *J. Membr. Sci.* 204(1&2):97-110 (2002).
Yoder, C., et al., "Reactions of the ambidentate substrate chloromethyldimethylchlorosilane with amines and amides," *J. Organ. Chem.* 190(1):1-7 (Apr. 1980).

* cited by examiner

*Primary Examiner*—H. Thi Le
(74) *Attorney, Agent, or Firm*—Dorsey & Whitney LLP; David J. Brezner (57) ABSTRACT

Polyfunctional silicon compounds of one of the following formula:

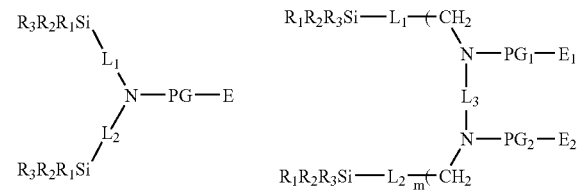

in which N-PG is a nitrogen containing function group. Also, such compounds bound to substrates for use as chromatography packing.

22 Claims, 6 Drawing Sheets

Figure 1

Figure 2     Amitriptyline Test

Figure 3 Polarity Test

POLAR SILANES FOR BINDING TO SUBSTRATES AND USE OF THE BOUND SUBSTRATES

BACKGROUND OF THE INVENTION

This invention relates to polyfunctional silicon compounds and to binding such compounds to substrates for uses such as a separation media. Conventional C18 (ODS) silica columns are widely accepted as general-purpose stationary phases. However, some drawbacks impede the use of these columns for certain applications, including the peak tailing of basic analytes and "phase collapse" (or "dewetting") in a highly aqueous environment. Recent advances in silica synthesis and bonding technology provide solutions to minimize the base tailing using high-density bonding followed by exhaustive end-capping of high purity silica. Densely bonded and highly hydrophobic ODS columns cannot be used in 100% water, since the "phase collapse" usually occurs, causing greatly reduced or irreproducible retention.

Polar-embedded phases were introduced in order to improve the peak shape of basic analytes and to make RP columns fully operational in highly aqueous environment. These phases are primarily hydrophobic but have hydrophilic groups incorporated near the silica surface. The commonly used polar groups are amide, urea, ether and carbamate functionalities. In general, the polar-embedded phases have the following benefits in comparison to conventional C18 packings: they provide good peak shapes of basic analytes, good compatibility with highly aqueous mobile phases, and selectivities that differ from those exhibited by general purpose C18 columns. On the other hand, the polar-embedded phases have their own drawbacks such as significantly decreased retention of basic and non-polar compounds and inferior hydrolytic stability, as compared to conventional C18 columns. Therefore, they are often complementary to C18 columns and operated in a narrower pH range.

Several processes have been developed to produce the hydrolytically stable silica based stationary phases. R. P. Fisk et al. (WO 00/45951) discloses a process for preparing the porous inorganic/organic hybrid silica particles as base solid support for further modifications. After reacting with the silylating agents, such as dimethyl octadecyl chlorosilane, the packing material is stated to demonstrate an enhanced hydrolytic stability within the 1–12 pH range. Another method for making stable silica packings for the HPLC applications, was developed by J. L. Glajch et al. (U.S. Pat. No. 4,705,725). It describes the stable support structures covalently modified by a mono-functional silane, containing two sterically hindered groups bound to a silicon atom. The columns packed with these materials are stated to show enhanced hydrolytic stability at low pHs. However, the use of bulky silylating agents could be disadvantageous, since bonded phases often have lower surface coverage, which may result in the decreased phase stability at elevated pHs. J. J. Kirkland et al. reported the preparation of bidentate silane stationary phases for reversed-phase HPLC (J. J. Kirkland; J. B. Adams, Jr.; M. A. van Straten; H. A. Claessens, *Analytic Chemistry*, 70: 4344–4352 (1998)). This packing material is stated to provide good hydrolytic stability within a broad range of pH levels (1.5–11.5) and to results in satisfactory column efficiency. G. MaGall (U.S. Pat. No. 6,262,216 B1) described the synthesis and use of polyfunctional silanes with tertiary amine groups containing one derivatizable functionality such as hydroxyl, amino, carboxyl, thio, halo and sulfonate, and two reactive silyl moieties.

An objective of this invention is to provide polyfunctional silylating agents with built-in polar fragments, which provide bonded silica phases with the benefits of the polar-embedded packings, and enhance their longevity. There is a need to provide improved polyfunctional silica compounds which can be used for HPLC stationary phase development.

SUMMARY OF THE INVENTION

One embodiment of the invention is a polyfunctional silicon compound having one of the following structures:

Formula I

Formula II wherein at least one of $R_1$, $R_2$ and $R_3$ is a leaving group which, after leaving, permits the Si in one of said structures to form a Si—O—Si or Si—O—Zr bond, wherein $L_1$, $L_2$ and $L_3$ comprise alkyl or substituted alkyl chains from 1 to 100 carbons in length, wherein m=1–100;

wherein N-PG, N-$PG_1$ and N-$PG_2$ are nitrogen-containing polar groups; and wherein each of E, $E_1$, and $E_2$ comprise alkyl, substituted alkyl, aryl, or substituted aryl groups, comprising 1–50 carbon atoms, and exclude functional groups selected from the group consisting of hydroxyl, carboxyl, amino, thio, halo and sulfonate moieties.

Another embodiment of the invention is a composition comprising a silicon compound covalently bound to a substrate having one of the following structures:

Formula III

-continued

Formula IV wherein at least one of $R_1$ and $R_2$ are independently an alkyl or substituted alkyl group or a leaving group which, after leaving, permits the Si in one of said structures to form a Si—O—Si or Si—O—Zr bond, wherein $L_1$, $L_2$, and $L_3$ comprise alkyl or substituted alkyl chains from 1 to 100 carbons in length, wherein m=1–100, wherein N-PG, N-PG$_1$ and N-PG$_2$ are nitrogen-containing polar groups, wherein each of E, $E_1$, and $E_2$ comprise alkyl, substitute alkyl or aryl or substituted aryl groups, comprising 1–50 carbon atoms, and exclude functional groups selected from the group consisting of hydroxyl, carboxyl, amino, thio, halo and sulfonate moieties.

In another embodiment, analytes in a liquid sample are separated by flowing through medium comprising the composition of the previous paragraph.

DETAILED DESCRIPTION OF THE PREFERRED EMBODIMENTS

A variety of silicon compounds, which are commercially available, or which can be synthesized as disclosed herein, can be used in the methods disclosed herein to react ith the surfaces of substrates to form functionalized substrates for a wide range of applications. In one embodiment, the silicon compounds are covalently attached to the surfaces of the substrates in order to modify those substrates with various functional groups. For example, the silicon compounds may be attached to the surface of silica gel to provide the functionalized silica particles for chromatographic packings.

As used herein, the term "silicon compound" refers to a compound comprising at least two silicon atoms and a polar-embedded functionality, such as amide, carbamate, sulfonamide, or urea. In a preferred embodiment, the silicon compound is a silylating agent comprising at least two activated silicon groups, such as hydroxy, alkoxy, halo, or aminosilane. These groups are capable of reacting with a functional group, for example, on a surface of a substrate, to form a covalent bond with a surface. The activated silicon groups of silicon compound can react with the surface of a substrate such as silica or zirconia, comprising the Si—OH or Zr—OH groups, respectively, to create the Si—O—Si or Si—O—Zr bonds between the silicon compound and a substrate. Exemplary activated silicon groups include but are not limited to —Si(OMe)$_3$; —SiMe(OMe)$_2$; —SiMe$_2$(OMe); —Si(OEt)$_3$; —SiMe(OEt)$_2$; —SiMe$_2$(OEt) and —SiCl$_3$, —SiMe$_2$N(Me)$_2$.

As used herein, the term "polyfunctional silicon compound" refers to a compound comprising at least two activated silyl groups and a polar-embedded functionality, such as amide, carbamate, sulfonamide, or urea. The general structures of these silicon compounds are the following:

Formula I

Formula II wherein at least one of $R_1$, $R_2$ and $R_3$ is a leaving group which, after leaving, permits the Si in one of said structures to form a Si—O—Si or Si—O—Zr bond, wherein $L_1$, $L_2$ and $L_3$ comprise alkyl or substituted alkyl chains from 1 to 100 carbons in length, wherein m=1–100;

wherein N-PG, N-PG$_1$ and N-PG$_2$ are nitrogen-containing polar groups; and wherein each of E, $E_1$, and $E_2$ comprise alkyl, substituted alkyl, aryl, and substituted aryl groups and exclude functional groups selected from the group consisting of hydroxyl, carboxyl, amino, thio, halo and sulfonate moieties. E, $E_1$ and $E_2$ comprise 1 to 50 carbon atoms, preferably 1 to 30 carbon atoms, and more preferably 1 to 20 carbon atoms.

In Formulas I and II, at least one of $R_1$, $R_2$, and $R_3$ is a leaving group which, after leaving, permits the Si in one of said structures to form a Si—O—Si or Si—O—Zr bond. Suitable leaving groups include hydroxy, alkoxy, halide, or amino group, for example, —OMe, or OEt. In one embodiment, $R_1$, $R_2$, $R_3$ are all —OMe. In another embodiment, $R_1$ and $R_2$ are independently a reactive group, such as hydroxy, alkoxy, halide, or amino group. For example, —OMe, or OEt, and $R_3$ may be an alkyl group, such as Me, or substituted alkyl group. In another embodiment, $R_1$ may be a reactive group, such as hydroxy, alkoxy, halide, or amino group. For example, —OMe, and $R_2$ and $R_3$ may be independently alkyl group, such as Me, or substituted alkyl group.

In Formulas I and II, $L_1$, $L_2$ and $L_3$, are independently alkyl or substituted alkyl chains, preferably —$(CH_2)_{n^-}$, of a carbon chain length of 1 to 100, preferably 1 to 50 in length. Groups $L_1$, $L_2$ and $L_3$ may contain heteroatoms such as nitrogen, oxygen, silicon, and sulfur. $L_3$ may contain aromatic and heteroaromatic fragments such as phenyl and pyridyl, respectively.

In Formulas I and II, in one embodiment, =N-PG is a nitrogen-containing polar-embedded functionality, also referred to as a polar group. Suitable polar groups include amide, carbamate, sulfonamide, or urea groups.

In Formulas I and II, E, $E_1$ and $E_2$ comprise a non-derivatizable functional group, specifically alkyl, substituted alkyl, aryl, substituted aryl groups, excluding functional groups selected from the group consisting of hydroxyl, carboxyl, amino, thio, halo, and sulfonate moieties.

In one embodiment, E, $E_1$ and $E_2$ comprise a cyano terminal moiety. E, $E_1$ and $E_2$ may comprise an alkyl chain of sufficient length so that when said silicon compound is bound to a substrate, it is capable of use as a reverse phase chromatography medium. E, $E_1$ and $E_2$ are molecular fragments consisting of 1 to 50 carbon atoms, preferably of 1 to 30 carbon atoms, and more preferably of 1 to 20 carbon atoms.

In Formula II, m=1 to 100, preferably 1 to 10. For example, when m=1, $L_1$=$L_2$=$L_3$=(—$CH_2$—)$_2$, the Formula II results in compounds 10 or 11 containing specific substituents.

Exemplary compounds of Formula I are as follows:

1

2

3

-continued

4

5

6

7

8

9

Exemplary Compounds of Formula II are as Follows:

One method for synthesizing polyfunctional silicon compounds of Formula I is a follows: Diallyl amine is first allowed to react with a reagent, such as acyl chloride, carbamoyl chloride, sulfonyl chloride, or isocyanate, containing a proper functionality. The resulting polar-embedded diallyl compound is then subjected to a hydrosilylation in presence of the silicon compound of formula $SiHR_1R_2R_3$ and a Pt catalyst to generate a polyfunctional silicon compound of Formula I.

Scheme 1 below provides an example of synthesizing the polyfunctional silicon compound of Formula I. Scheme 1 shows the synthesis of silicon compound 1.

SCHEME 1

An alternative method for making polyfunctional silicon compounds is based on the commercially available aminosilanes, such as bis(trimethoxysilylpropyl)amine (Scheme 2). Scheme 2 shows the synthesis of silicon compound 3.

SCHEME 2

The synthesis of silicon compounds of Formula II can be carried out similarly, in accordance with the methods of Schemes 1 and 2.

In one embodiment, the silicon compounds of Formulas I or II are bound to a substrate, preferably for use as a chromatography separation medium as in a packed bed form.

In a particular embodiment, the substrate comprises a silica surface. The hydrolytic stability of functional layer bound to a silica surface can be enhanced by increasing the number of covalent bonds between the silica surface and a deposited functional layer. General structures of novel functional layers with more than one point of attachment to a silica substrate, are illustrated by Formula III and Formula IV below:

Formula III

Formula IV wherein $R_1$ and $R_2$ are independently an alkyl or substituted alkyl group or a leaving group which, after leaving, permits the Si in one of said structures to form a Si—O—Si or Si—O—Zr bond, wherein $L_1$, $L_2$, and $L_3$ comprise alkyl or substituted alkyl chains from 1 to 100 carbons in length, wherein m=1–100, wherein N-PG, N-$PG_1$ and N-$PG_2$ are nitrogen-containing polar groups, wherein each of E, $E_1$, and $E_2$ comprise alkyl, substituted alkyl, aryl, substituted aryl groups and exclude functional groups selected from the group consisting of hydroxyl, carboxyl, amino, thio, halo and sulfonate moieties. E, $E_1$, and $E_2$ are molecular fragments comprising 1 to 50 carbon atoms.

Suitably, the silicon compound is covalently bound to a substrate, wherein the Si groups attached to $L_1$ and $L_2$ are covalently bound to the substrate by reaction of $R_1$, $R_2$ or $R_3$ of Si of said $L_1$ $S_1$ or $L_2$—Si linkages with reactive groups on said substrate selected from the group consisting of silanol, alkoxysilane, halosilane and aminosilane moieties.

The polyfunctional silicon compounds can be covalently attached to a variety of substrates. Exemplary substrates include materials that comprise a functional group that is capable of reacting with the polyfunctional silicon compounds containing activated silyl groups. Thus, the polyfunctional silicon compounds can be attached, for example, to the silica based materials such as glass surfaces, or the surfaces of other silicon oxide, titanium oxide, germanium oxide, zirconium oxide, and aluminum oxide based materials; and also to the surfaces of various carbonized materials, metals, crosslinked and non-crosslinked polymers, which contain suitable functional groups for reacting with the invented silicon compounds. The examples of the above mentioned suitable functional groups are silanols, alkoxysilanes, titanium hydroxides, zirconium hydroxides, etc. Developed silicon compounds can also be incorporated into the polymeric or sol-gel networks by utilizing the reactive silicon functionalities. Compounds of formulas I and II, containing polymerizable groups or groups that can be converted into radicals and/or ion-radicals, and/or ions, can be used for making polymeric materials and for surface grafting, by utilizing those groups and/or reactive silicon functionalities. The resulting materials can be applied for a development of adsorbents, membranes, filters, microfluidic devices, microchips, and functionalized surfaces for various types of separation, detection, and analysis. This invention will be particularly applied to a development of new stationary phases for various chromatographic separations, and reversed phase separations, in particular.

In one embodiment, the mono- and multi-layered surfaces are prepared by treating silica substrates with the polyfunctional silicon compounds of Formulas I and II. Such silicon compounds can be covalently attached to a variety of substrates, such as silica gel, zirconia, hybrid sol-gel/polymers or glass plates. Suitable silica gels comprise nonporous, or porous silica particles of different pore sizes, preferably from 20 Å to 3000 Å, and more preferably from 60 Å to 2000 Å; and of different particle sizes, preferably from 0.2 um to 1000 um, and more preferably from 2 um to 50 um. The treatment reaction can be carried out in a slurry of silica gel in an inert solvent, such as toluene, at elevated temperature. Water, acid or base catalyst can be applied to enhance the surface coverage, depending on the type of properties desired for the separation media.

Alternatively, an aminosilane compound, such as bis(trimethoxysilylpropyl)amine can be used for modifying the underivatized silica gel by incorporating the reactive amino group onto a surface. Then, a reagent, such as acyl chloride, carbamyl chloride, sulfonyl chloride, or isocyanate, containing a proper functional group, can be reacted with the aminated silica gel to form the corresponding bonded phase. The synthetic route for this transformation is illustrated in Scheme 3. Scheme 3 illustrates an alternative procedure (two-step synthesis) for modification of silica support with new polar-embedded ligands.

This invention provides a simple and versatile approach to produce a variety el solid supports with excellent hydrolytic stability. The method of synthesis allows for efficient incorporation of different functionalities onto the surfaces of the substrates and silica substrates, in particular. The resulting materials can be applied for development of adsorbents, membranes, filters, microfluidic devices, microchips, and functionalized surfaces for various types of separation, detection and analysis. This invention can be applied to a development of new stationary phases for various chromatographic separations and reversed phase chromatography, in particular.

The following examples are offered solely for the purpose of illustration, and are intended neither to limit nor to define the invention.

EXAMPLE 1

This example illustrates a process for the synthesis of novel polyfunctional silicon compounds.

Synthesis of N,N-Bis(allyl) Polar-Embedded Precursors:

Diallyl amine was mixed with the excess of $Et_3N$ (2.0 equiv.) in $CH_2Cl_2$ and kept at 0° C. for 20 min. Then, a solution of acyl chloride, sulfonyl chloride or isocyanate (1.0 equiv) in $CH_2Cl_2$ was slowly added and the reaction mixture was stirred at ambient temperature for 12 hours. The reaction mixture was washed with water and dried over $Na_2SO_4$. After removal of all volatiles under reduced pressure, the corresponding N,N-bis(allyl) polar-embedded precursor was obtained. In the case when an isocyanate was used, the corresponding N,N-bis(allyl) urea-embedded precursor was obtained by mixing an isocyanate with diallyl amine in toluene. The structures of synthesized compounds were confirmed by $^1$H NMR spectroscopy and mass spectrometry.

Synthesis of N,N-Bis(propylsilyl) Polyfunctional Silicon Compound:

An N,N-bis(allyl) polar-embedded precursor was added to a mono-, di- or triethoxysilane (2 to 20 molar excess of silane). Then a catalyst (0.1 mol %), such as hexachloroplatinic acid in a minimum amount of ethanol was introduced into the reaction mixture. After stirring at 50° C. for 24 hours, the excess of volatiles was removed under reduced pressure to yield corresponding N,N-bis(propylsilyl) polyfunctional silicon compound. The structures of synthesized compounds were confirmed by $^1$H NMR spectroscopy and mass spectrometry.

EXAMPLE 2

This example illustrates an alternative process for the synthesis of novel polyfunctional silicon compounds when N,N-bis(silyl)amines, such as bis(trimethoxysilylpropyl) amine or bis[(3-trimethoxysilyl)propyl]ethylene diamine were used as starting materials.

An alternative synthesis of polyfunctional silicon compounds.

An N,N-bis(silyl)amine, such as bis(trimethoxysilylpropyl)amine or bis[(3-trimethoxysilyl)propyl]ethylene diamine was mixed with the excess of $Et_3N$ (2.0 equiv.) in $CH_2Cl_2$ and was kept at 0° C. for 20 min. Then, a solution of acyl chloride, sulfonyl chloride or isocyanate (1.0 equiv) in $CH_2Cl_2$ was slowly added and the reaction mixture was stirred at ambient temperature for 4 hours. The reaction mixture was washed with water and dried over $Na_2SO_4$. After removal of all volatiles under reduced pressure, the corresponding polyfunctional silicon compound was obtained. In the case when an isocyanate was used, the corresponding urea-embedded silane ligand was obtained by mixing an isocyanate with N,N-Bis(silyl)amine in toluene. The structures of synthesized compounds were confirmed by $^1$NMR spectroscopy and mass spectrometry.

EXAMPLE 3

This example illustrates a process for silica functionalization using novel polyfunctional silicon compounds.

General Procedure for Silica Functionalization:

The reaction was carried out in the slurry of selected silica gel and a polyfunctional silicon compound in the inert solvent such as toluene, at elevated temperature. Water, acid or base catalyst can be applied to control the surface coverage of the functionalized silica gel, depending on a particular application. In order to produce a packing material for chromatographic separation, an appropriate end-capping or other type of post-derivatization reaction can be used if necessary.

EXAMPLE 4

This example describes the chromatographic evaluation of octadecylamide functionalized silica produced from the polyfunctional silicon compound 3. Synthesized samples were prepared from high-purity raw silica gel with the following physical properties: average particle size, 5.0 μm; specific surface area, 295 m$^2$/g; mean pore size, 136 Å; pore volume, 1.00 mL/g; Bonded silica was packed into 4.6×150 mm stainless steel columns using traditional high-pressure slurry techniques.

Figure 1:
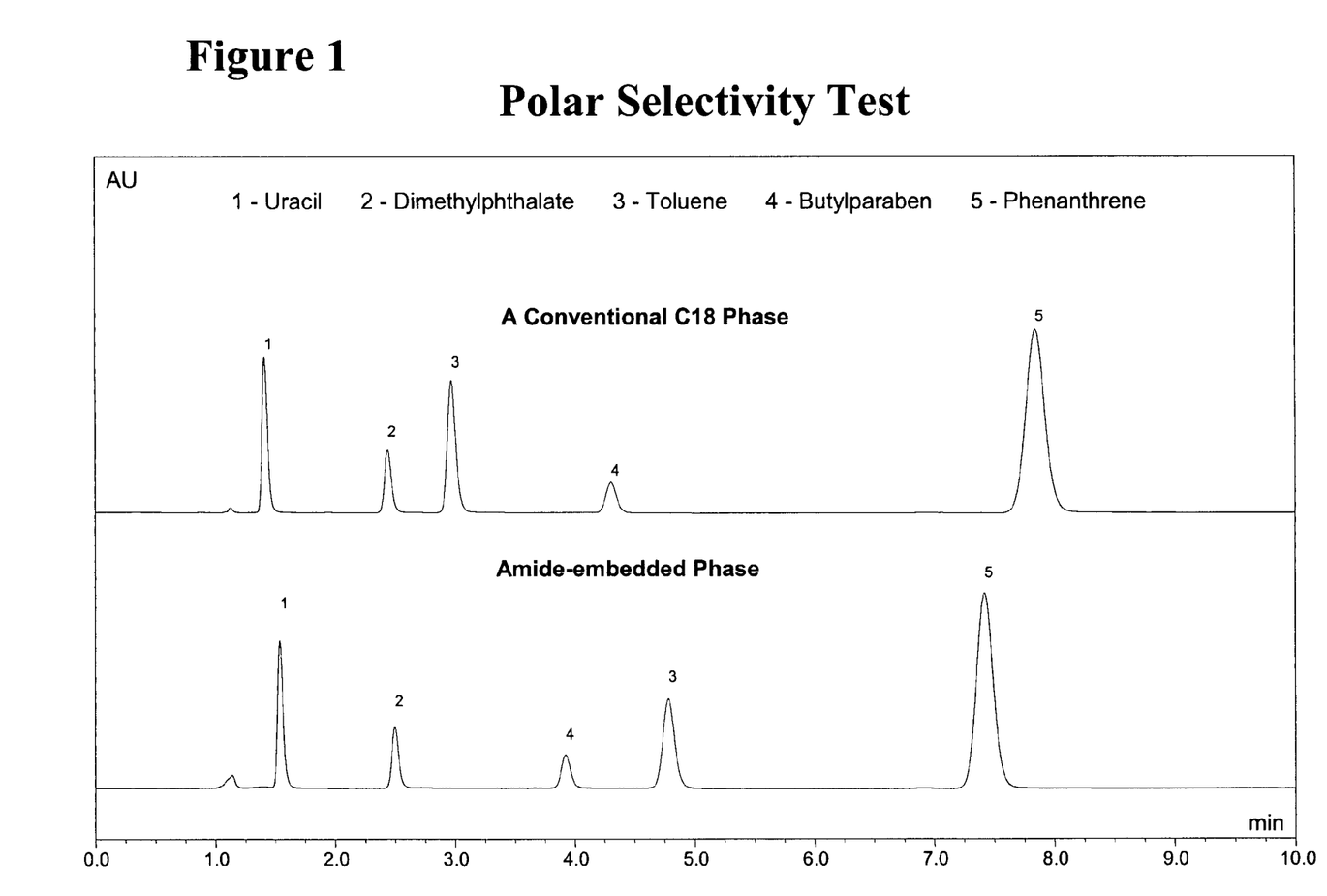
FIG. 1 illustrates the polar selectivity test comparison using conventional C18 phase and newly developed amide-embedded C18 phase.

Polar Selectivity Test:

The test standard was a mixture of uracil, dimethylphthalate, butylparaben, toluene and phenanthrene. The test conditions were: eluent, $CH_3CN/H_2O$ (70:30 v/v); flow rate, 1 mL/min; injection volume, 5 μL; temperature, 30° C.; and detection, 254 nm. FIG. 1 shows that the new phase has different selectivity as compared to conventional RP C18 materials, displaying different elution order for toluene and butylparaben analytes.

Amitriptyline Test:

The test mix contained uracil, toluene, ethylbenzene, amitriptyline and quinizarin. The test conditions were: eluent, MeOH/20 mM $K_2HPO_4/KH_2PO_4$ (80:20 v/v); flow rate, 1 mL/min; injection volume, 5 μL; temperature, 30° C.; and detection, 254 nm.

Figure 2:
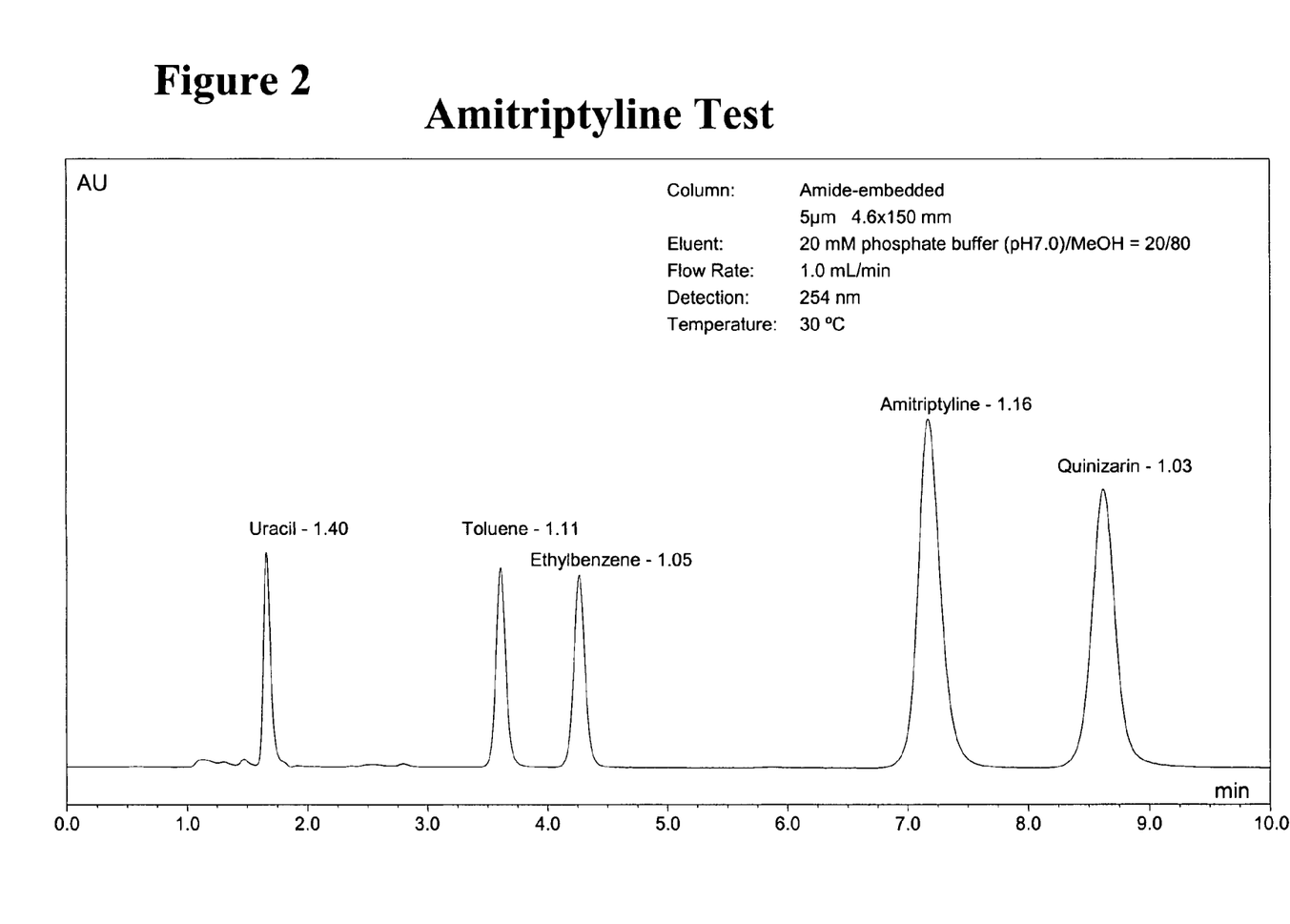
FIG. 2 illustrates the amitriptyline test using newly developed amid-embeded embedded C18 phase.

Aminotriptyline (pKa=9.3) test conducted with pH 7 mobile phase, is a sensitive method for monitoring silanol activity. At this pH, many of the residual silanols are negatively charged, and the basic probes are completely protonated. The protonated base molecules interact with the ionized silanols via ion-exchange mechanism, thus the degree of tailing is a direct measure of silanol activity. As shown in FIG. 2, the new phase provides excellent peak shape and low asymmetry for amitriptyline ($AS_{amitriptyline}$<1.2), which indicates that the polar moiety incorporated into the new phase reduces the interaction between bases and residual silanols quite effectively.

Figure 3:
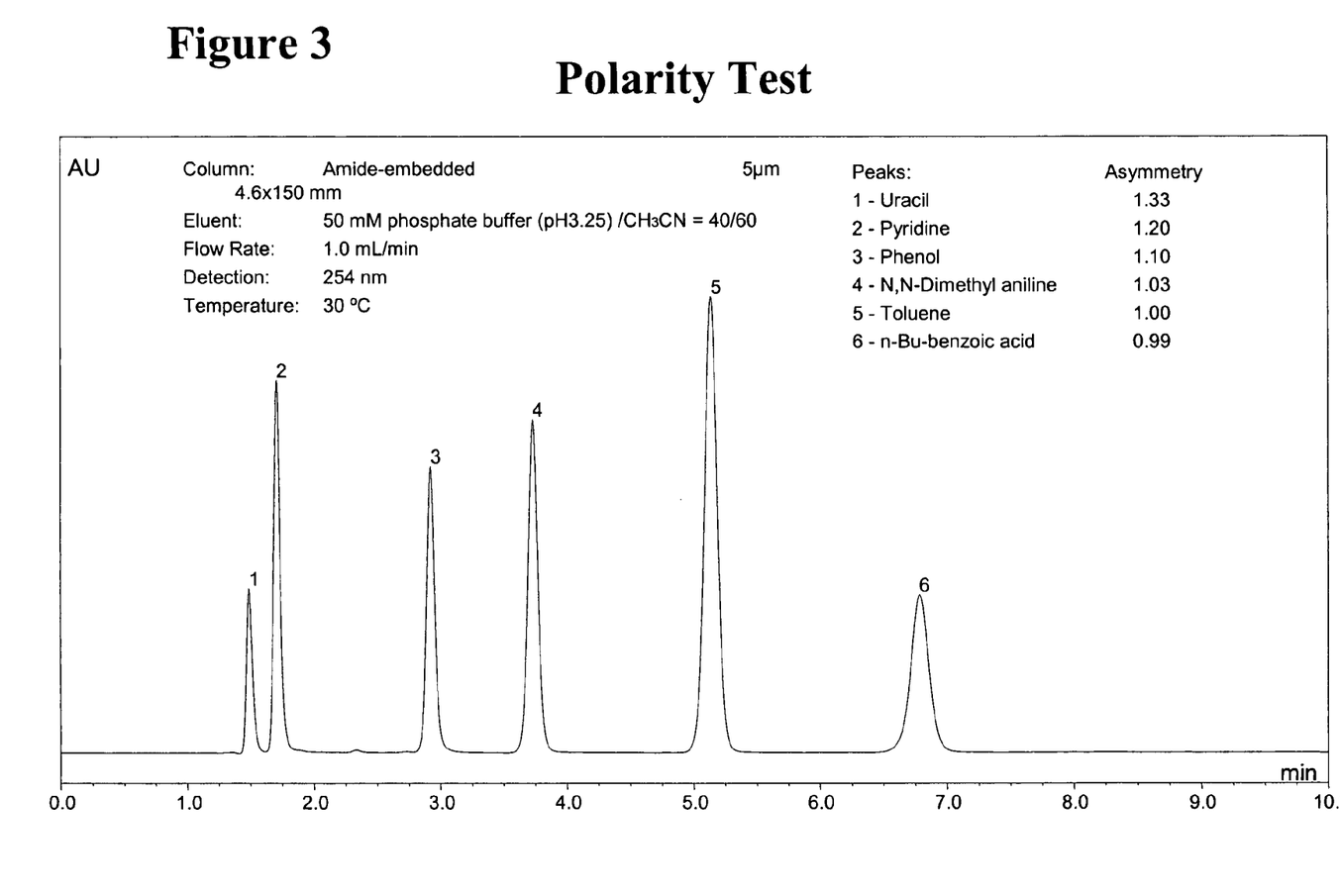
FIG. 3 illustrates the polarity test using newly developed amide-embedded c18 phase.

Polarity Test:

The test mixture contained uracil (void marker), pyridine (basic), phenol (acidic), N,N-dimethyl aniline (basic), p-butylbenzoic acid (acidic), and toluene (non-polar). The test conditions were: eluent, $CH_3CN/50$ mM $K_2HPO_4/KH_2PO_4$ (60:40 v/v; flow rate, 1 mL/min; injection volume, 5 μL; temperature, 30° C.; and detection, 254 nm. The test results are shown in FIG. 3. It was shown that excellent peak shapes for all acid, basic, and non-polar analytes, can be achieved on the new amide-embedded phase, suggesting good overall column performance.

Phase Collapse Test:

The bonded phase was tested in a 10 mM $H_3PO_4$, pH 2.4 mobile phase at 30° C. A freshly packed column was washed with 50 column volumes of $CH_3CN$, and then equilibrated with 100 column volumes of a mobile phase. The sample solution contained cytosine, uracil and thymine. In the stop-flow experiment, each test cycle consisted of two steps. Step one: the column was equilibrated with a mobile phase for 20 min, then the sample was injected and the data acquisition was conducted for another 10 min. Step two: flow was stopped for 30 min before starting the next cycle. Fifty cycles were performed for each bonded phase.

Figure 4:
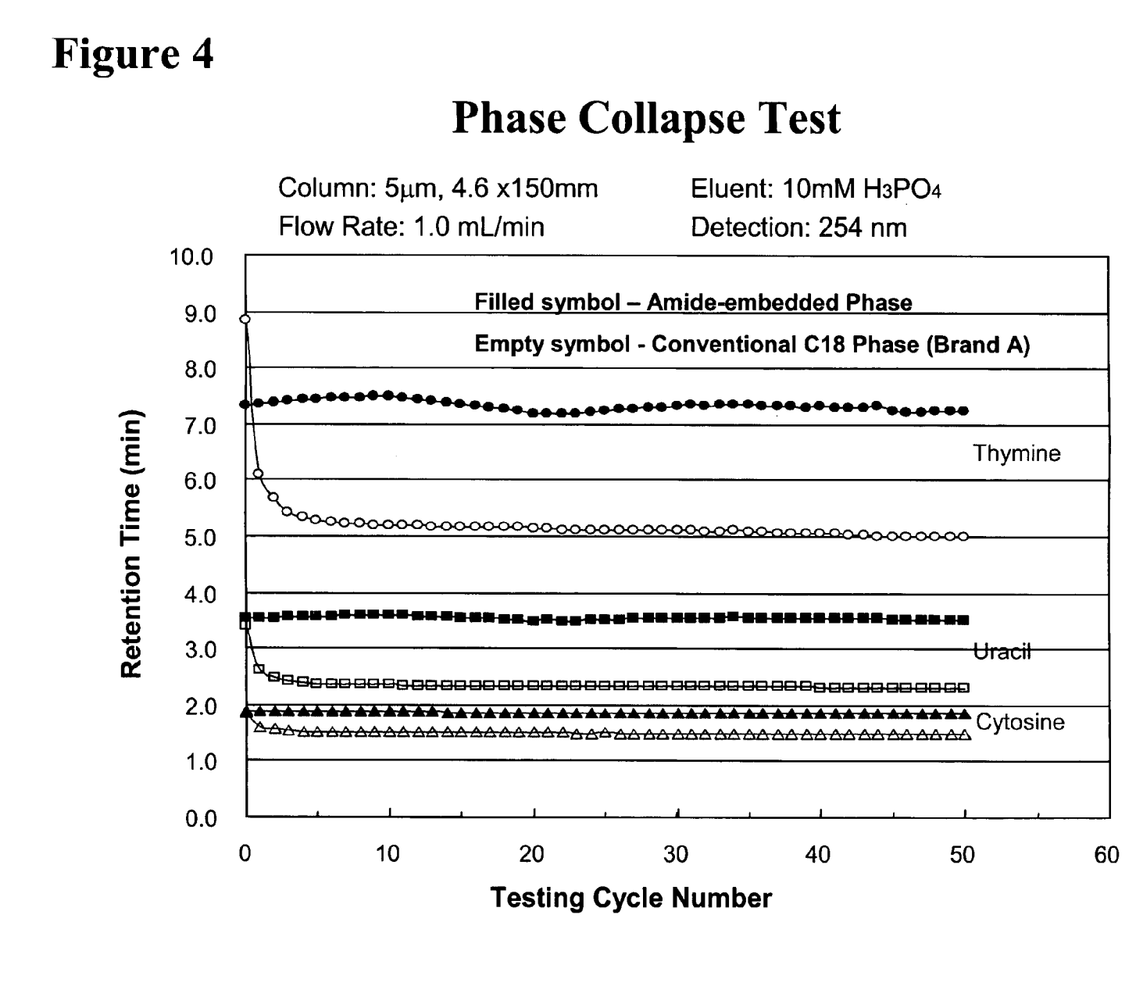
FIG. 4 illustrates the phase collapse test using newly developed amide-embedded C18 phase in comparison to a conventional C18 column.

A newly developed amide-embedded phase was compared against a fresh commercial high-density C18 phase (Brand A) using the "stop-flow" test in a 100% aqueous eluent (FIG. 4). It was found that the high-density C18 column suffered a sudden loss of retention for cytosine, uracil and thymine after the first stop-flow cycle (FIG. 4). Further gradual decrease of retention was observed in the following cycles. In comparison, the newly developed amide-embedded phase performed consistently well under the same conditions. The only negligible loss of retention was observed after fifty stop-flow cycles for all three analytes (less than 1.0, 1.0, and 5.0% retention drops for cytosine, uracil, and thymine, respectively).

Hydrolytic Stability Test

The bonded silica columns were tested with $CH_3CN/1\%$ TFA, pH1 (50:50 v/v) mobile phase at 50° C. and $CH_3CN/20$ mM $Et_3N$ pH 11.5 (50:50 v/v) eluent at 30° C. First, a freshly packed or purchased column was washed with 50 column volumes of $CH_3CN$, then equilibrated with 50 column volumes of a mobile phase. The sample solution contained uracil and toluene. The k value for toluene was measured using the average of two injections. The column was purged with a mobile phase at a flow rate of 1 mL/min and periodically re-tested during 10 to 30 days.

Figure 5:
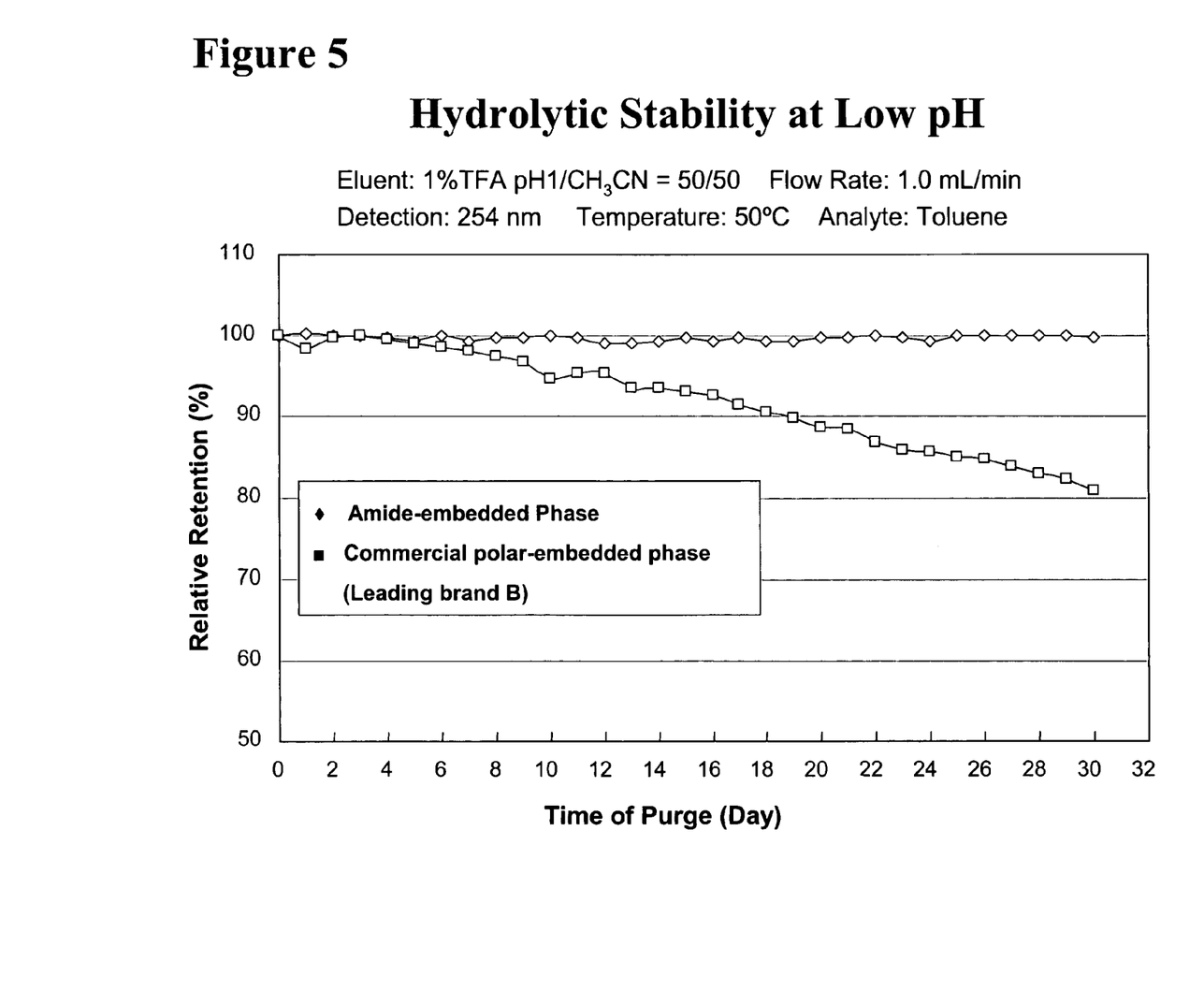
FIG. 5 illustrates the hydrolytic stability test at pH1 and 50° C. using newly developed amide-embedded C18 column and a well-known polar-embedded commercial phase (brand B).

The new amide phase and a well-known polar-embedded commercial phase (brand B) were subjected to low pH stability test at pH 1 and 50° C. During a 30-day testing period, less than 1% drop of toluene k was observed for a new phase, while nearly 20% drop of k value occurred when brand B column was tested under the same conditions (FIG. 5). The increased number of covalent bonds between the functional silicon compound and a silica surface is believed to be the main reason for an excellent stability of the new amide polar-embedded phase described in this invention.

Figure 6:
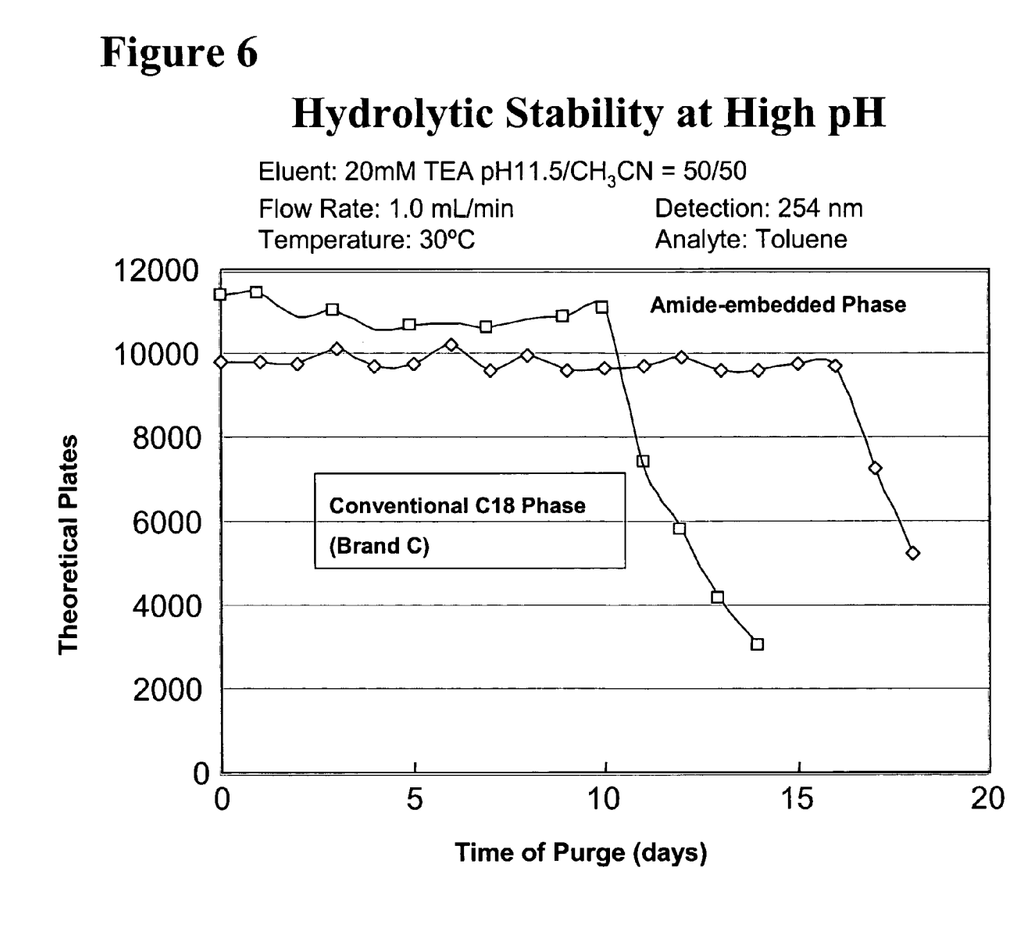
FIG. 6 illustrates the hydrolytic stability test at pH 11.5 and 30° C. using newly developed amide-embedded C18 column and high-density conventional C18 phase (brand C).

A new amide polar-embedded phase was compared against a high-density C18 phase prepared on a base of the same raw silica gel, using high pH stability test at pH 11.5, 30° C. (FIG. 6). It was found that the high-density C18 phase failed after ten days of continuous purging, due to column bed collapse. In comparison, the new amide phase was stable for sixteen days under the same conditions, which is translated into approximately 60% increase of stability. Since multiple bonds were formed between each ligand molecule and the silica surface, and because certain degree of crosslinking was most likely achieved, the functional layer of the developed amide-embedded phase had a stabilizing effect, preventing a rapid dissolution of the silica backbone at elevated pHs.

The methods described in this invention serve as a platform for the development of various stationary phases with enhanced hydrolytic stability and complimentary chromatographic characteristics including the following.

1. Enhanced hydrolytic stability at both low and high pHs
2. Compatibility with 100% aqueous eluents
3. Different selectivity from conventional C18 reversed-phases
4. Low peak asymmetry for both basic and acidic analytes
5. High phase capacity that provides the retention of hydrophobic analytes similar to high-density conventional C18 column.

What is claimed is:

1. A polyfunctional silicon compound having one of the following structures:

wherein at least one of $R_1$, $R_2$ and $R_3$ is a leaving group which, after leaving, permits the Si in one of said structures to form a Si—O—Si or Si—O—Zr bond,
wherein $L_1$, $L_2$ and $L_3$ comprise alkyl or substituted alkyl chains from 1 to 100 in length,
wherein m=1–100;
wherein N-PG, N-$PG_1$ and N-$PG_2$ are nitrogen-containing polar groups;
wherein each of E, $E_1$, and $E_2$ comprise alkyl, substituted alkyl, aryl, or substituted aryl groups, comprising 1–50 carbon atoms, and exclude functional groups selected from the group consisting of hydroxyl, carboxyl, amino, thio, halo and sulfonate moieties.

2. The silicon compound of claim 1 wherein E, $E_1$, and $E_2$ comprise a cyano terminal moiety.

3. The silicon compound of claim 1 wherein, when bound to a substrate, E, $E_1$, and $E_2$ comprise an alkyl chain of sufficient length so that when said silicon compound is bound to a support, it is capable of use as reverse phase chromatography medium.

4. The silicon compound of claim 1 in which E, $E_1$ and $E_2$ comprise an alkyl chain of at least 1 carbon in length.

5. The silicon compound of claim 1 wherein N-PG is selected from the group consisting of an amide, a carbamate, a sulfonamide and urea.

6. The silicon compound of claim 1 in which $R_1$, $R_2$ or $R_3$ is selected from the group consisting of hydroxyl, alkoxy, halide and amino moieties.

7. The silicon compound of claim 1 covalently bound to a substrate, wherein the Si groups attached to $L_1$ and $L_2$ are covalently bound to the substrate by reaction of $R_1$, $R_2$ or $R_3$ of Si of said $L_1$—$S_1$ or $L_2$—Si linkages with reactive groups on said substrate selected from the group consisting of silanol, alkoxysilane, halosilane and aminosilane moieties.

8. The silicon compound of claim 7 in which said substrate comprises silica gel.

9. The silicon compound of claim 7 in which said substrate comprises glass.

10. The silicon compound of claim 7 in which said substrate comprises a sol-gel or hybrid sol-gel/polymer.

11. The silicon compound of claim 1 having the following structure:

12. The silicon compound of claim 1 having the following structure:

13. A composition comprising a silicon compound covalently bound to a substrate having one of the following structures:

wherein at least one of $R_1$ and $R_2$ are independently an alkyl or substituted alkyl group or a leaving group which, after leaving, permits the Si in one of said structures to form a Si—O—Si or Si—O—Zr bond, wherein m=1–100;

wherein N-PG, N-$PG_1$ and N-$PG_2$ are nitrogen-containing polar groups;

wherein each E, $E_1$, and $E_2$ comprise alkyl, substituted alkyl, aryl or substituted aryl groups, comprising 1–50 carbon atoms, and exclude functional groups selected from the group consisting of hydroxyl, carboxyl, amino, thio, halo and sulfonate moieties.

14. The composition of claim 13 wherein N-PG is selected from the group consisting of an amide, a carbamate, a sulfonamide and urea.

15. The composition of claim 13 wherein said substrate is a silica substrate.

16. The composition of claim 13 wherein said silica substrate comprises a silica gel.

17. The composition of claim 13 in which said substrate comprises a sol-gel or hybrid sol-gel/polymer.

18. The composition of claim 13 in a flow-through bed suitable for use as reverse phase chromatography separation medium.

19. The composition of claim 13 having the following structure:

20. The composition of claim 13 having the following structure:

21. A chromatographic method comprising flowing an aqueous liquid stream through a bed of separation medium comprising the composition of claim 13.

22. A method for the chromatographic separation of analytes in a liquid sample comprising flowing said liquid sample through medium comprising the composition of claim 13.

* * * * *

UNITED STATES PATENT AND TRADEMARK OFFICE
CERTIFICATE OF CORRECTION

PATENT NO. : 7,074,491 B2
APPLICATION NO. : 10/702109
DATED : July 11, 2006
INVENTOR(S) : Liu et al.

It is certified that error appears in the above-identified patent and that said Letters Patent is hereby corrected as shown below:

Col. 3, line 39, delete "amid-embeded embedded", and insert -- amide-embedded --.

Col. 3, line 41, delete "c18", and insert -- C18 --.

Col. 3, line 58, delete "ith", and insert -- with --.

Col. 9, line 19, delete "$L_1S_1$", and insert -- $L_1Si$ --.

Col. 11, line 40, delete "$^1$NMR", and insert -- $^1$H NMR --

Signed and Sealed this

Fifth Day of December, 2006

JON W. DUDAS
*Director of the United States Patent and Trademark Office*